United States Patent [19]

Perricone

[11] Patent Number: 5,409,693
[45] Date of Patent: Apr. 25, 1995

[54] METHOD FOR TREATING AND PREVENTING SUNBURN AND SUNBURN DAMAGE TO THE SKIN

[76] Inventor: Nicholas V. Perricone, 350 Cosey Beach Ave., East Haven, Conn. 06512

[21] Appl. No.: 24,890

[22] Filed: Mar. 1, 1993

Related U.S. Application Data

[63] Continuation of Ser. No. 732,444, Jul. 18, 1991, abandoned, which is a continuation of Ser. No. 420,287, Oct. 12, 1989, abandoned.

[51] Int. Cl.$^6$ .......... A61K 7/40; A61K 7/42; A61K 7/48
[52] U.S. Cl. .................. 424/59; 514/474; 514/887; 514/938
[58] Field of Search .............. 424/59, 60; 514/725, 514/938, 887, 474

[56] References Cited

U.S. PATENT DOCUMENTS

| | | | |
|---|---|---|---|
| 2,377,188 | 5/1945 | Schwenk et al. | 424/60 |
| 4,670,263 | 6/1987 | Noorlander | 424/195.1 |
| 4,695,452 | 9/1987 | Gannes et al. | 514/725 |
| 4,818,521 | 4/1989 | Tamabuchi | 514/938 |
| 4,919,921 | 4/1990 | Hatae | 424/62 |
| 4,975,272 | 12/1990 | Voyt | 514/887 |
| 4,983,382 | 1/1991 | Willmott et al. | 424/62 |
| 5,021,452 | 6/1991 | Labbe et al. | 514/474 |

FOREIGN PATENT DOCUMENTS

| | | | |
|---|---|---|---|
| 2744976 | 4/1979 | Germany | 514/474 |
| 4523634 | 8/1970 | Japan | 514/474 |
| 0120612 | 9/1981 | Japan | 424/62 |
| 0116616 | 6/1985 | Japan | 514/474 |
| 0116618 | 6/1985 | Japan | 514/474 |
| 1152613 | 7/1986 | Japan | 424/63 |
| 468628 | 9/1975 | U.S.S.R. | 514/474 |

OTHER PUBLICATIONS

Harry, The Principles and Practice of Modern Cosmetics, 1963, vol. One, pp. 197–200, 204, 215, 219–221.

*Primary Examiner*—Dale R. Ore
*Attorney, Agent, or Firm*—St. Onge Steward Johnston & Reens

[57] ABSTRACT

A method for the therapeutic treatment of skin disorders of the type directly or indirectly caused by collagen deficiency, and/or oxygen-containing free radicals and/or by oxidative generation of biologically active metabolites, in which a fat-soluble fatty acid ester of ascorbic acid is topically applied to the affected skin areas, preferably in association with a dermatologically acceptable carrier.

13 Claims, No Drawings

METHOD FOR TREATING AND PREVENTING SUNBURN AND SUNBURN DAMAGE TO THE SKIN

This is a continuation of application Ser. No. 07/732,444 filed on Jul. 18, 1991, abandoned, which is a continuation of Ser. No. 07/420,287 filed Oct. 12, 1989, now abandoned.

BACKGROUND OF THE INVENTION

The present invention relates primarily to a method for the therapeutic treatment of skin disorders, and more particularly to a topical application method, and compositions for use therein, for treating disorders of the skin which are caused by, or are dependent upon, depleted or inadequate collagen levels, and/or oxygen-containing free radicals, and/or oxidative generation of active metabolites via lipoxygenase pathways.

A wide variety of skin diseases and skin conditions in which the skin has undergone some form of damage or accelerated aging can be traced, either directly or indirectly, to processes which either deplete or inhibit synthesis of collagen, and/or generate oxygen-containing free radicals, and/or oxidatively generate biologically active metabolites, generally via lipoxygenase pathways, which in turn either directly act upon the skin or mediate other processes which have adverse effect on the skin. Such is the case, for example, in radiation-induced skin damage, particularly ultraviolet radiation-induced skin damage (e.g., sunburn), where it appears possible that the transfer of energy from the radiation to the skin results in the generation of excited oxygen species, such as singlet oxygen, the superoxide anion, and hydroxyl radicals, that can damage lipid-rich membranes with the subsequent activation of the chemical mediators of inflammation and/or damage the skin cell membrane and DNA, and also where it appears that the radiation releases arachadonic acid which is then oxidized via two predominant pathways to produce either prostaglandins or leukotrines. Such is also the case for skin damage resulting from chronic exposure to sunlight as well as in the natural aging process, where free radical-induced damage appears to be involved and where collagen content is diminished. Such also is the case for disease conditions such as psoriasis, a chronic, recurrent, scaling skin disease of unknown etiology, where it is possible that hydro-eicosatetraenoic acids and leukotrines generated by oxidation of arachidonic acid via the lipoxygenase pathway have a role in the pathogenesis of the disease.

An equally wide variety of therapeutic and/or prophylactic treatments have been suggested for preventing and/or alleviating skin conditions or diseases or collagen deficiencies. Critical to the success of any such methodology is the utilization of an active ingredient or ingredients which is effective for its purpose without concurrent generation of adverse side effects. Equally important, however, is the ability to employ an active ingredient which can be effectively delivered to the sites where it will act most efficaciously on the disease or condition (or afford protection therefrom). Generally speaking, it is thus necessary for the active ingredient to be deliverable in either an intact form or in a form whereby the active ingredient is exposed or released in the actual environment where its activity is needed. So too, it is of importance that the active ingredient be such as to be compatible with a base composition which facilitates topical application and which facilitates application in suitable dosages, and further that the active ingredient either be stable per se or have the ability to be stabilized in admixture with other components, so that preparations can be marketed with a suitably long shelf-life and such that prolonged activity can be obtained once topical application has been made.

In large part, known treatment and prevention methodologies for skin diseases and conditions fail in one or more of these criteria. Thus, known compounds which at least in theory might be useful in treating a skin disorder of the type described herein, either have potentially adverse side effects and/or cannot be delivered in active form and/or cannot be solubilized in base compositions and/or are unstable. See, e.g., Kaplan, D. L., et al., Journal Of Cutaneous Aging & Cosmetic Dermatology, Vol. 1, No. 2 (1988/89), incorporated herein by reference. As such, the need very much exists for provision of a useful methodology for treatment and/or prevention of skin disorders in which collagen deficiency, and/or oxygen-containing free radicals, and/or biologically active products of oxidative processes are involved.

SUMMARY OF THE INVENTION

In accordance with the present invention, ascorbic acid (Vitamin C), in the form of its fat-soluble fatty acid esters (e.g., ascorbyl palmitate, ascorbyl laurate, ascorbyl myristate, ascorbyl stearate and the like), and preferably in association with a dermatologically acceptable carrier in which it is dispersed or solubilized, is topically applied in effective amounts to skin areas which have been damaged or aged, or which are susceptible to damage, by reason of mechanisms which are dependent upon, or which involve, collagen deficiency, and/or oxygen-containing free radicals, and/or biologically active metabolites of oxidative processes (particularly those generated via the lipoxygenase pathway). Typical skin disorders of this type are radiation (especially ultraviolet)-induced skin burn, psoriasis, aging (and associated thinning of the dermis), and the like.

It has been found in accordance with the invention that ascorbic acid, in the form of its fat-soluble fatty acid esters, is effective in the treatment of skin conditions and diseases which are caused by, or depend upon, or otherwise involve, collagen deficiency, and/or oxygen-containing free radicals and/or the oxidative generation of biologically active metabolites (e.g., prostaglandins, hydroeicosatetraenoic acids, leukotrines); can be delivered, either alone or in association with a carrier, into lipid-rich skin layers without loss of efficacy; can be employed without adverse side effects; is stable against oxidation when exposed to air, a property which can be enhanced with use of a carrier for the ascorbyl fatty acid ester; and which can be employed in a wide variety of carriers either to enhance overall effectiveness or percutaneous delivery or stability. In addition, synergistic activity often noted in the use of Vitamin C along with fat-soluble vitamins such as Vitamin E, which synergism traditionally acts only at aqueous-lipid interfaces, can be further enhanced in accordance with the invention by reason of extension of that activity beyond water-lipid interfaces and into wholly or predominantly lipid layers.

In the preferred practice of the invention, the ascorbyl fatty acid ester is applied in admixture with a dermatologically acceptable carrier or vehicle (e.g., as a lotion, cream, ointment, soap, or the like) so as to facilitate topical application and, in some cases, provide additional therapeutic effects as might be brought about, e.g., by moisturizing of the affected skin areas. In this way it is also possible to provide preparations which can be applied in a regimen which provides a suitable and controlled dosage of the ascorbyl fatty acid ester with each application.

The amount of the ascorbyl fatty acid ester necessary to bring about the therapeutic treatment of the skin disorder is not fixed per se, and necessarily is dependent upon the particular disorder, its severity and extent, the particular ascorbyl fatty acid ester employed, and the concentration of the ascorbyl fatty acid ester when employed in association with a carrier. Generally, the ascorbyl fatty acid ester or composition containing it is topically applied to the affected skin areas in a predetermined or as-needed regimen to bring about improvement, it generally being the case that gradual improvement is noted with each successive application. Insofar as has been determined based upon clinical studies to date, no adverse side effects are encountered.

When a carrier is employed, it is necessary that the carrier be inert in the sense of not bringing about a deactivation of the ascorbyl fatty acid ester, and in the sense of not bringing about any adverse effect on the skin areas to which it is applied.

Suitable carriers include water, alcohols, oils and the like, chosen for their ability to dissolve or disperse the active ingredient at concentrations of active ingredient most suitable for use in the therapeutic treatment. Generally, even low concentrations of active ingredient in a carrier will be suitable, requiring only that more frequent topical application be resorted to. As a practical matter, however, to avoid the need for repeated application, it is desirable that the topically applied composition (i.e., ascorbyl fatty acid ester plus carrier) be formulated to contain at least about 0.5% by weight, more preferably at least about 2% by weight, and most preferably at least about 10% by weight, of the active ingredient, and accordingly, carriers will be chosen which can solubilize or disperse the active ingredient at such concentrations.

While the carrier for the ascorbyl fatty acid ester can consist of a relatively simple solvent or dispersant such as water or oils, it is generally preferred that the carrier comprise a composition more conducive to topical application, and particularly one which will form a film or layer on the skin to which it is applied so as to localize the application and provide some resistance to washing off by immersion in water or by perspiration and/or one which aids in percutaneous delivery and penetration of the ascorbyl fatty acid ester into lipid layers. Many such compositions are known in the art, and can take the form of lotions, creams, gels or even solid compositions (e.g., stick-form preparations). Typical compositions include lotions containing water and/or alcohols and emollients such as hydrocarbon oils and waxes, silicone oils, vegetable, animal or marine fats or oils, glyceride derivatives, fatty acids or fatty acid esters or alcohols or alcohol ethers, lanolin and derivatives, polyhydric alcohols or esters, wax esters, sterols, phospholipids and the like, and generally also emulsifiers (nonionic, cationic or anionic), although some of the emollients inherently possess emulsifying properties. These same general ingredients can be formulated into a cream rather than a lotion, or into gels, or into solid sticks by utilization of different proportions of the ingredients and/or by inclusion of thickening agents such as gums or other forms of hydrophillic colloids. Such compositions are referred to herein as dermatologically acceptable carriers. Most preferred are those carriers which are fat-soluble, i.e., those which can effectively penetrate skin layers and deliver the active ascorbyl fatty acid ester to the lipid-rich layers of the skin.

DETAILED DESCRIPTION OF THE INVENTION

As earlier noted, specific applications of the present invention involve psoriasis and radiation-induced skin damage (including natural aging), both of which are postulated to involve oxygen-containing free-radical generation and/or oxidative generation of biologically active metabolites. Other important applications of the invention involve use of the topically-applied ascorbyl fatty acid esters to aid in or accelerate collagen synthesis, so as to remedy conditions which arise because of depleted collagen or inhibited collagen synthesis.

Psoriasis is presently without cure, and the course and remission of the disease are unpredictable, even capricious. Current therapeutic regimens include topical or intralesional application of corticosteroids, topical administration of anthralin or keratolytics, and use of tar and UV light on affected areas. These many treatments all have their benefits and drawbacks, and many factors must be considered in the choice of therapy. No single therapy is ideal, and it is rare for a patient not to be treated with several alternatives during the relapsing and remitting course of the disease. Whereas systematic treatment can induce prompt resolution of psoriatic lesions, suppression often requires ever-increasing doses, sometimes with toxic side effects, and tapering of therapy may result in rebound phenomena with extensions of lesions, possibly to exfoliation.

Information representing the current state of the art with respect to psoriasis and its treatment can be found in, e.g., Lowe, Nicholas J., Practical Psoriasis Therapy, Year Book Medical Publishers, Chicago, 1986, pp. 11–13; Mier, Paul D., and van de Kerhof, Peter C. M., eds., Textbook of Psoriasis, Churchill Livingstone, New York, 1986, pp. 13–39, 167 et seq; and Wyngaarden, James B., and Smith, Lloyd H., Cecil's Textbook of Medicine, W. B. Saunders Co., Philadelphia, 1988, pp. 2326–2327.

In a clinical program designed to test the effectiveness of the present invention, a composition was prepared consisting of 75 weight percent lecithin and 25 weight percent ascorbyl palmitate.

Twelve patients were examined in the study, five women and seven men, ranging in age from 19 to 71 years. All patients had psoriasis vulgaris plaque type varying in severity, and all had been using topical steroids for over six months with minimal benefit. The previously-described composition was applied to selected plaques once daily under occlusion using an (Squibb & Co.) Actiderm dressing, while other selected plaques were treated at the same time intervals with lecithin alone, also under occlusion with Actiderm dressing. The patients were examined at weekly intervals and assessed for clinical improvement. While some degree of improvement (seen as a thinning of plaques, and decrease in scaling and erythema) was noted for the areas treated with the control composition, dramatically better improvement was noted for the areas treated with the ascorbyl palmitate-containing composition. The average improvement over a period of two weeks of therapy was 60% for the ascorbyl palmitate-containing composition.

With regard to radiation-induced skin damage, and particularly skin burn brought about by excessive exposure to ultraviolet radiation (either sunlight or artificial UV sources such as used in tanning booths or incident to application of UV radiation as part of a therapeutic treatment), the clinical manifestations of ultraviolet induced burn seen in acute reactions is caused by ultraviolet radiation in the range of 290-320 nanometers, generally designated ultraviolet B (UVB) radiation. In artificial light sources, shorter wave lengths are also responsible for producing delayed erythema. It is now known that the longer wave lengths, i.e., 320-400 nanometers, designated UVA, in larger doses can also cause erythema. Included in the acute reactions of solar radiation is pigmentation. This immediate pigmentation reaction is caused by the ultraviolet radiation in the range of 320 nanometers and above. There is a delayed pigmentation reaction seen a few days after exposure, and finally there is seen an increase in thickness of the epidermis a few days after exposure, which is apparently some protective mechanism against subsequent sun exposure. The chronic reactions seen in exposure to ultra violet radiation are premature aging of the skin due to prolonged exposure to ultraviolet radiation (this is seen clinically as irregularly distributed pigmentation and thickening of the skin) and premalignant and malignant growths of the skin.

The cause of sunburn is postulated to be a transfer of energy from ultraviolet radiation to the skin, resulting in generation of excited oxygen species, such as singlet oxygen, the superoxide anion, and hydroxyl radicals that can damage lipid-rich membranes with the subsequent activation of the chemical mediators of inflammation. It is well known that ultraviolet B radiation releases arachadonic acid, which is quickly oxidized to a variety of biologically active metabolites, such as prostaglandins PGD2, PGE2, PGEF2. When arachadonic acid is oxidized via the cyclo-oxygenase pathway, prostaglandins create marked erythema. Arachadonic acid oxidized via the 5-lipo-oxygenase pathway produces leukotrines, which also can cause erythema and edema. The free radicals created by ultraviolet radiation can also damage the DNA of the cells, resulting in permanent injury, premature aging, and carcinogenesis.

The clinical symptoms of ultraviolet burn are on a spectrum from mild increased sensitivity of the skin to severe pain. It should also be noted that damage to skin can be caused by other forms of radiation, that is, ionizing radiation as well as longer wave length radiation such as infrared, which can result in erythema and pigmentation as well as premature aging and malignancy. These other forms of radiation create damage by the same mechanism, i.e., generation of free radicals with subsequent damage to the cell membrane and DNA.

Suggestions for dealing with sunburn and other forms of ultraviolet radiation burn have predominantly been aimed at prevention rather than treatment. Several topical sunscreens have been developed, and have proved to be very effective in preventing sunburn and long-term photo-damage. However, these agents must be used prior to ultraviolet exposure in order to exert their protective effect.

In order to demonstrate the efficacy of ascorbyl fatty acid esters in treatment of radiation skin burn, a composition was prepared in which ascorbyl palmitate was mixed with a cream which contained 1,000 mg of ascorbyl palmitate per 30 g of cream. The emollient cream included the components of Stearic acid, Isopropyl myristate, Polyoxyl 40 Stearate, Stearyl alcohol, Xanthan gun, Sorbic acid, Butylated hydroxytoluene, purified water, and Diazolidinyl urea. The test subjects were five Caucasians, three women and two men. Their backs were covered with paper, with two windows 3 cm by 3 cm exposing skin on the left and right mid back. They were then irradiated using a high pressure metal halide lamp with broad spectrum UVB—UBA emission. Three hours after irradiation, obvious erythema appeared on the back at the two exposed sites. At that time, the subjects were asked to begin application of cream to these areas every four hours during their waking time. They were given two jars of cream, one marked "L" meaning left side of back, one marked "R" designating right side of back. They were asked to apply these appropriately to the erythematous lesions. One jar contained the emollient cream with the ascorbyl palmitate. The other jar contained the emollient cream without active ingredient. The subjects were instructed to dispense approximately one gram of cream per application. The subjects were then observed by a dermatologist at 24 hrs. and then daily for a total of three days. At the follow-up observation by the dermatologist rated at 24 hrs., a 50% reduction in erythema was noted on the side utilizing the cream with the ascorbyl palmitate content. At 48 hrs., the erythema observed on the side using the active ingredient had faded to almost imperceptible pinkness, while the side treated with the base only still had marked erythema and edema. The subjects all reported marked reduction in symptoms of burn on the side treated with active ingredient.

The effectiveness of the ascorbyl fatty acid esters in the treatment of psoriasis and of radiation-induced skin damage and of other like diseases and conditions can be postulated as resulting from the anti-oxidant properties of ascorbic acid per se, which properties are retained to a high degree in the ascorbyl fatty acid ester form, together with the fact that the ascorbyl fatty acid ester form is capable of being delivered in an effective manner. Thus, when solubilized in the lipid-rich layers of the skin, the fatty acid ester form of ascorbic acid is capable of scavenging free oxygen-containing radicals, neutralizing other reactive oxidants released extracellularly and intracellularly, and either interfering with or minimizing oxidative generation of metabolities via lipoxygenase pathways.

Generally speaking, the present invention is one which involves the topical application of fat-soluble fatty acid esters of ascorbic acid as a means for bringing about and/or augmenting any or all of the effects or actions which ascorbic acid normally brings about in vivo, i.e., its role in the synthesis of collagen, its role as a free radical scavenger or neutralizer, its role as an inhibitor of the lipoxygenase oxidation pathway (i.e., as a result of being a cyclooxygenase agonist), and the like. By virtue of the fat-solubility of these fatty acid esters and the further enhancement of this solubility via admixture with fat-penetrating carriers, the active ascorbic acid can be effectively percutaneously delivered to lipid layers so as to bring about these effects and actions, and further can be utilized in forms which protect it against oxidative loss of activity. In turn, since many skin conditions and diseases, such as psoriasis and radiation-induced cutaneous burn, appear to be dependent upon mechanisms or deficiencies which the actions and effects of ascorbic acid can counteract, the present invention offers a means for directly treating such disorders.

Having described the invention with reference to particular compositions, theories of effectiveness, and the like, it will be apparent to those of skill in the art that it is not intended that the invention be limited by such illustrative embodiments or mechanisms, and that modifications can be made without departing from the scope or spirit of the invention, as defined by the appended claims.

What is claimed is:

1. A method for treating skin sunburn comprising topically applying to the skin sunburn a fatty acid ester of ascorbic acid effective to solubilize in the lipid-rich layers of the skin an amount effective to scavenge therefrom free radicals present as a result of transfer of energy to the skin from the ultraviolet radiation which produced said sunburn.

2. A method according to claim 1 wherein said fatty acid ester of ascorbic acid is topically applied to said skin sunburn in the form of a composition comprising said fatty acid ester of ascorbic acid and a dermatologically acceptable carrier.

3. A method according to claim 2 wherein said fatty acid ester of ascorbic acid is selected from the group consisting of ascorbyl palmitate, ascorbyl laurate, ascorbyl myristate, ascorbyl stearate and mixtures thereof.

4. A method according to claim 3 wherein said fatty acid ester of ascorbic acid is ascorbyl palmitate.

5. A method according to claim 4 wherein said composition comprises at least about 2% ascorbyl palmitate by weight.

6. A method according to claim 5 wherein said composition comprises at least about 10% ascorbyl palmitate by weight.

7. A method according to claim 2 wherein said composition further comprises Vitamin E.

8. A method for preventing sunburn damage to exposed skin surfaces, comprising topically applying to said skin surfaces a fatty acid ester of ascorbic acid effective to solubilize in the lipid-rich layers of the skin in an amount effective to scavenge therefrom free radicals generated by reason of transfer of energy to the exposed skin surfaces from the ultraviolet radiation of sunlight.

9. A method according to claim 8 wherein said fatty acid ester of ascorbic acid is topically applied to said exposed skin surfaces in the form of a composition comprising said fatty acid ester of ascorbic acid and a dermatologically acceptable carrier.

10. A method according to claim 9 wherein said composition comprises at least about 10% by weight of said fatty acid ester of ascorbic acid.

11. A method according to claim 10 wherein said fatty acid ester of ascorbic acid is selected from the group consisting of ascorbyl palmitate, ascorbyl stearate, ascorbyl laurate, ascorbyl myristate and mixtures thereof.

12. A method according to claim 11 wherein said fatty acid ester of ascorbic acid is ascorbyl palmitate.

13. A method according to claim 9 wherein said composition further comprises Vitamin E.

* * * * *